US006783514B2

(12) United States Patent
Tovey et al.

(10) Patent No.: US 6,783,514 B2
(45) Date of Patent: *Aug. 31, 2004

(54) FIBRIN SEALANT APPLICATOR

(75) Inventors: H. Johnathan Tovey, Monroe, CT (US); Ernie Aranyi, Easton, CT (US); Vinod C. Nagori, Trumbull, CT (US); Stanley Marczyk, Stratford, CT (US)

(73) Assignee: United States Surgical Corporation, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/792,535

(22) Filed: Jan. 31, 1997

(65) Prior Publication Data

US 2001/0016709 A1 Aug. 23, 2001

(51) Int. Cl.[7] .......................... A61M 5/00; A61M 37/00; A61M 5/178; B67D 5/60
(52) U.S. Cl. ......................... 604/191; 604/82; 604/216; 604/232; 222/145.1
(58) Field of Search ............................. 604/191, 181, 604/187, 185, 204, 212, 213, 214, 215, 216, 217, 232, 234, 153, 131, 133, 142, 148, 71, 73, 82; 222/92–104, 145.1, 129, 633

(56) References Cited

U.S. PATENT DOCUMENTS

| | | | |
|---|---|---|---|
| 1,948,388 A | | 2/1934 | Liberson |
| 2,112,160 A | | 3/1938 | Johnson |
| 2,576,766 A | * | 11/1951 | Sokolik ..................... 604/215 |
| 3,269,389 A | * | 8/1966 | Meurer et al. .............. 604/191 |
| 3,467,096 A | | 9/1969 | Horn |

(List continued on next page.)

FOREIGN PATENT DOCUMENTS

| | | |
|---|---|---|
| EP | 0 815 802 A2 | 1/1998 |
| EP | 0 830 900 A2 | 3/1998 |
| EP | 0 835 667 A1 | 4/1998 |
| EP | 0 858 776 A2 | 8/1998 |
| WO | 98/02098 | 1/1998 |
| WO | 98/10703 | 3/1998 |
| WO | 98/10704 | 3/1998 |
| WO | 98/13094 | 4/1998 |
| WO | 98/40115 | 9/1998 |
| WO | 98/40167 | 9/1998 |

*Primary Examiner*—Brian L. Casler
*Assistant Examiner*—Catherine S. Williams

(57) ABSTRACT

An applicator is provided for dispensing a first and a second component of a biological adhesive. The applicator includes a housing having a housing head for enclosing therein a first reservoir containing the first component, and a second reservoir containing the second component. The housing further includes an elongated body portion defining a longitudinal axis for enclosing therein a conduit assembly having a first and a second conduit in communication with the first and second reservoir, respectively. An activator assembly is provided which includes an activator and a rachet mechanism for compressing the reservoirs within the housing for dispensing the biological components into the conduits. An applicator tip having two separate channels in communication with the conduits may be provided on a distal end of the elongated body portion for dispensing the components on the application site. The first and second components are preferably fibrinogen and thrombin which intermix to form a fibrin sealant.

14 Claims, 16 Drawing Sheets

U.S. PATENT DOCUMENTS

| | | | |
|---|---|---|---|
| 3,502,078 A | * 3/1970 | Hill et al. | 604/94 |
| 3,552,394 A | 1/1971 | Horn | |
| 4,040,420 A | 8/1977 | Speer | |
| 4,121,739 A | 10/1978 | Devaney et al. | |
| 4,226,235 A | 10/1980 | Sarnoff et al. | |
| 4,260,077 A | 4/1981 | Schroeder | |
| 4,359,049 A | 11/1982 | Redl et al. | |
| 4,465,476 A | 8/1984 | Gähwiler | |
| 4,631,055 A | 12/1986 | Redl et al. | |
| 4,673,395 A | 6/1987 | Phillips | |
| 4,692,157 A | * 9/1987 | Landau et al. | 604/214 |
| 4,734,261 A | 3/1988 | Koizumi et al. | |
| 4,735,616 A | 4/1988 | Eibl et al. | |
| 4,874,368 A | 10/1989 | Miller et al. | |
| 4,902,281 A | 2/1990 | Avoy | |
| 4,950,245 A | * 8/1990 | Brown et al. | 604/153 |
| 4,978,336 A | 12/1990 | Capozzi et al. | |
| 4,979,942 A | * 12/1990 | Wolf et al. | 604/83 |
| 5,116,315 A | 5/1992 | Capozzi et al. | |
| 5,226,877 A | * 7/1993 | Epstein | 604/35 |
| 5,290,259 A | 3/1994 | Fischer | |
| 5,308,334 A | * 5/1994 | Sancoff | 604/131 |
| 5,328,462 A | * 7/1994 | Fischer | 604/191 |
| 5,368,563 A | 11/1994 | Lonneman et al. | |
| 5,376,079 A | 12/1994 | Holm | |
| 5,409,465 A | 4/1995 | Boggs et al. | |
| 5,464,396 A | 11/1995 | Barta et al. | |
| 5,474,540 A | 12/1995 | Miller et al. | |
| 5,520,658 A | 5/1996 | Holm | |
| 5,582,596 A | 12/1996 | Fukunaga et al. | |
| 5,584,811 A | * 12/1996 | Ross et al. | 604/141 |
| 5,643,206 A | * 7/1997 | Fischer | 604/191 |
| 5,665,067 A | * 9/1997 | Linder et al. | 604/191 |
| 5,848,730 A | * 12/1998 | Kawase et al. | 222/94 |
| 6,527,749 B1 | * 3/2003 | Roby et al. | 604/191 |

* cited by examiner

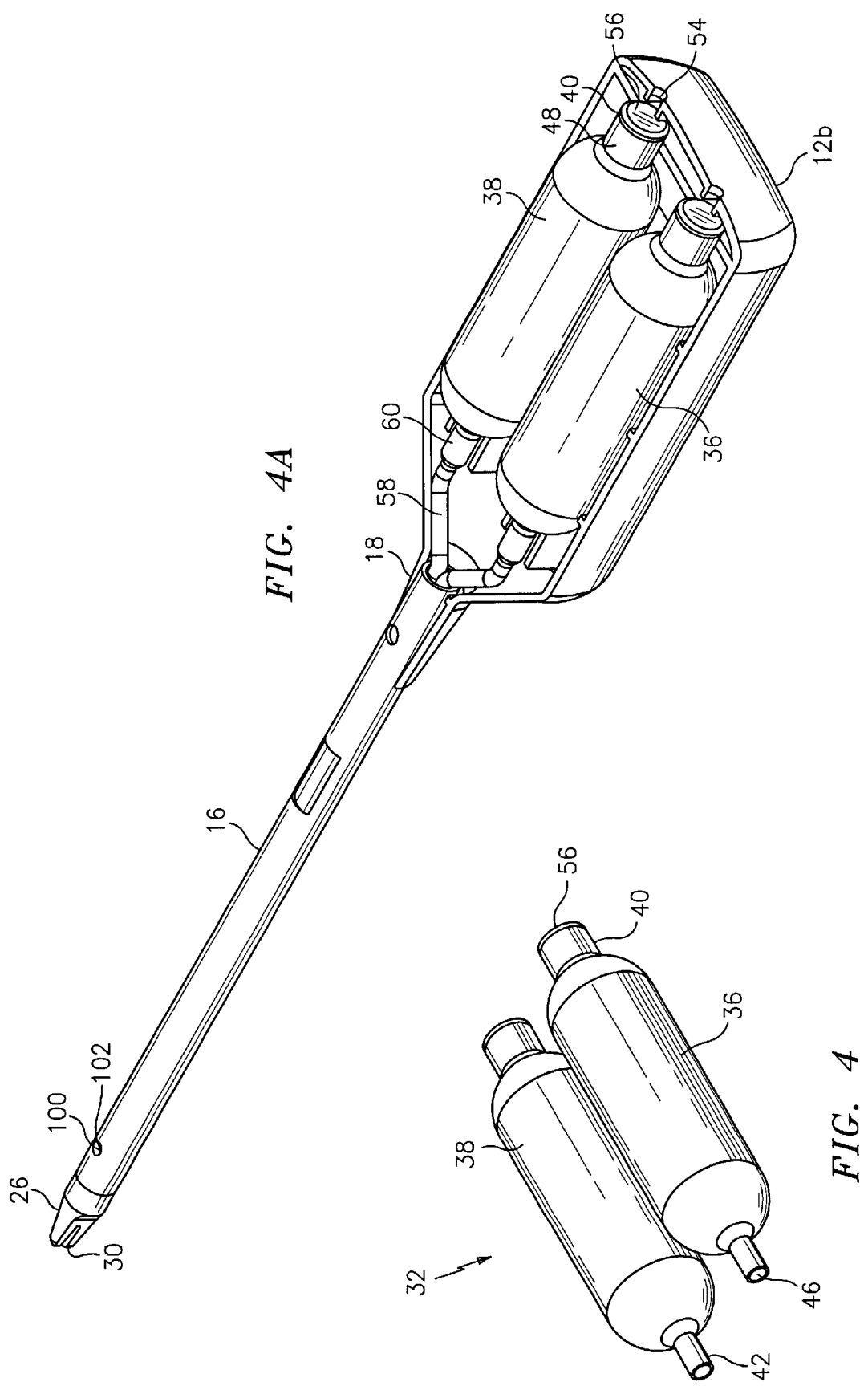

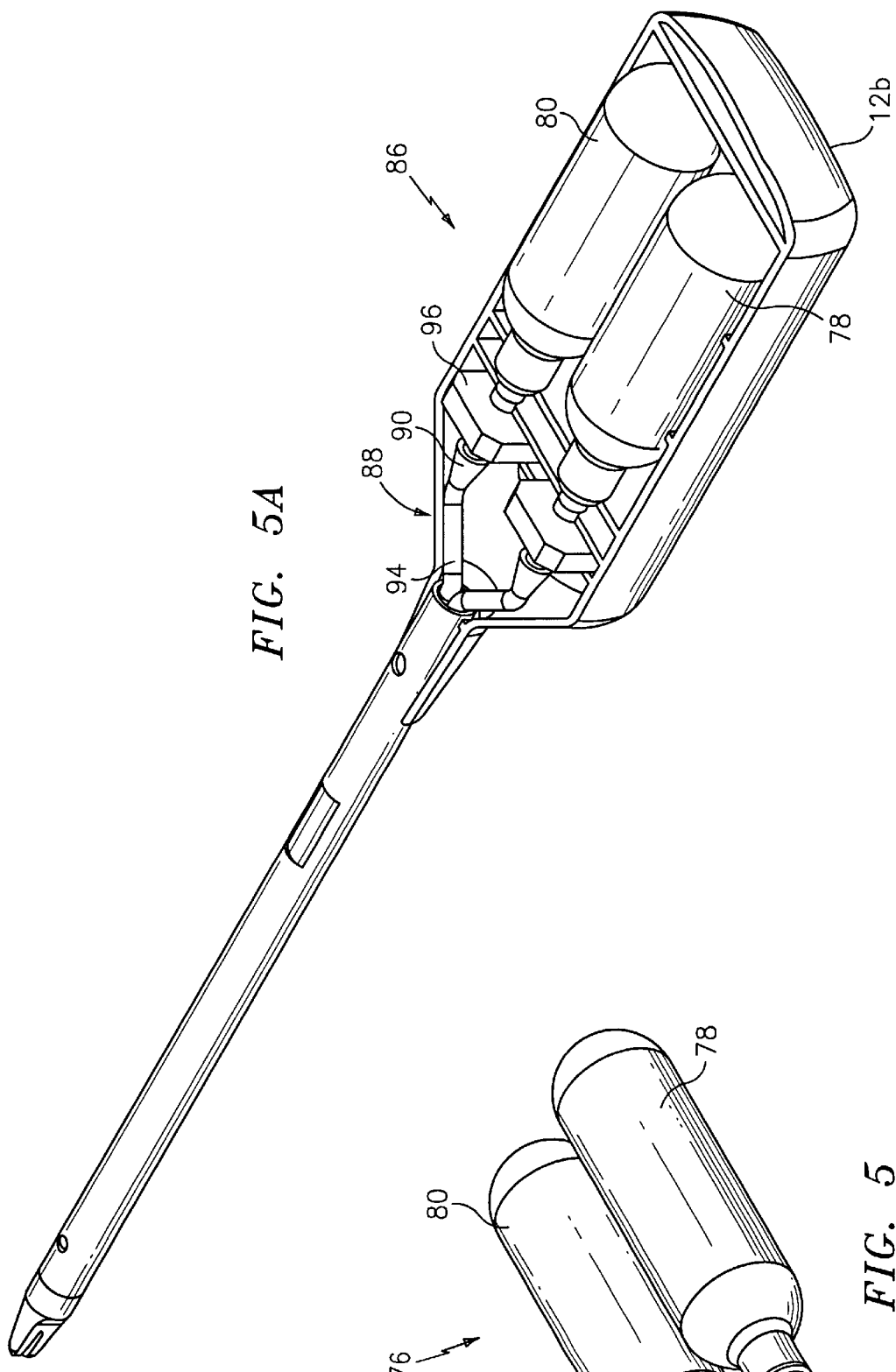
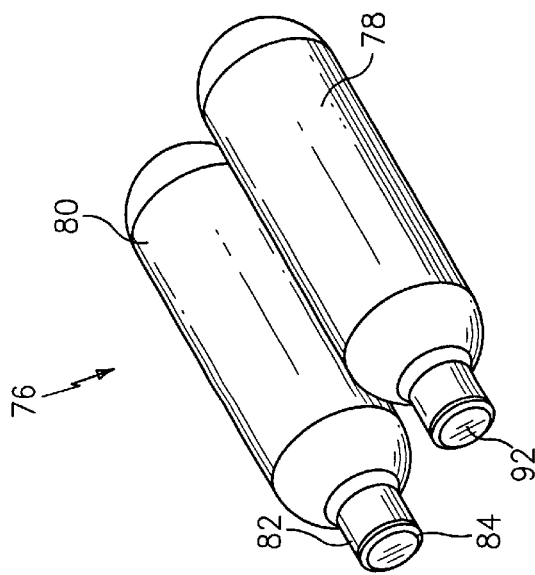

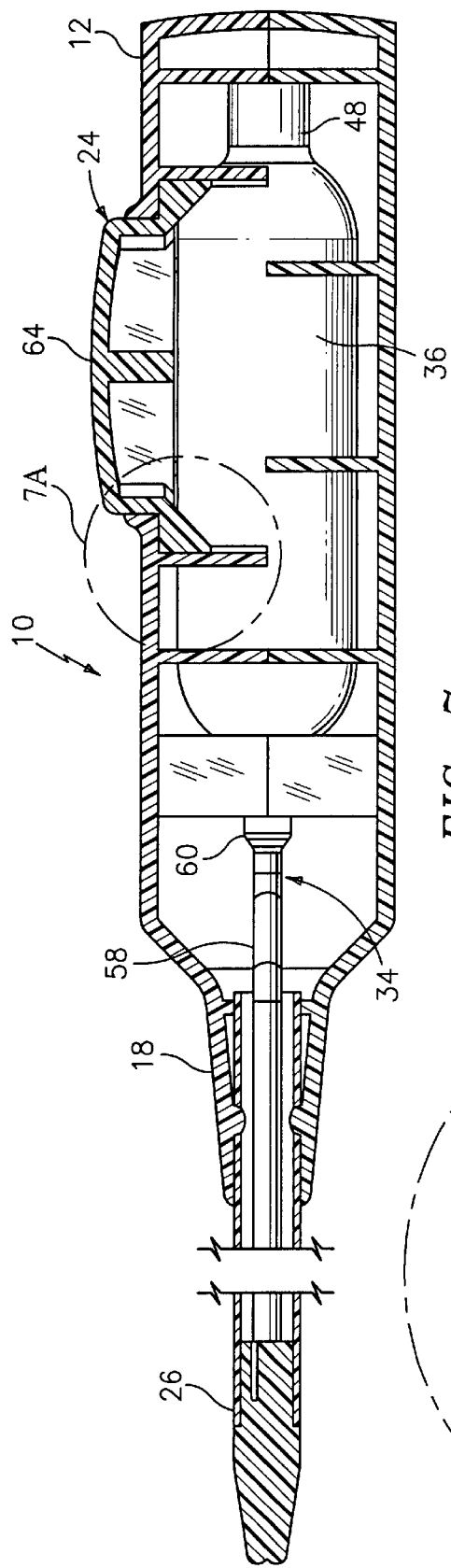
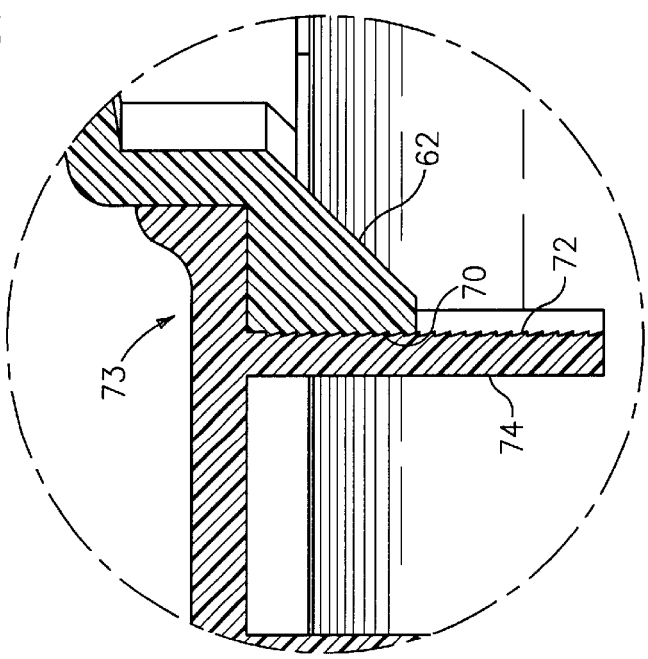
FIG. 7
FIG. 7A

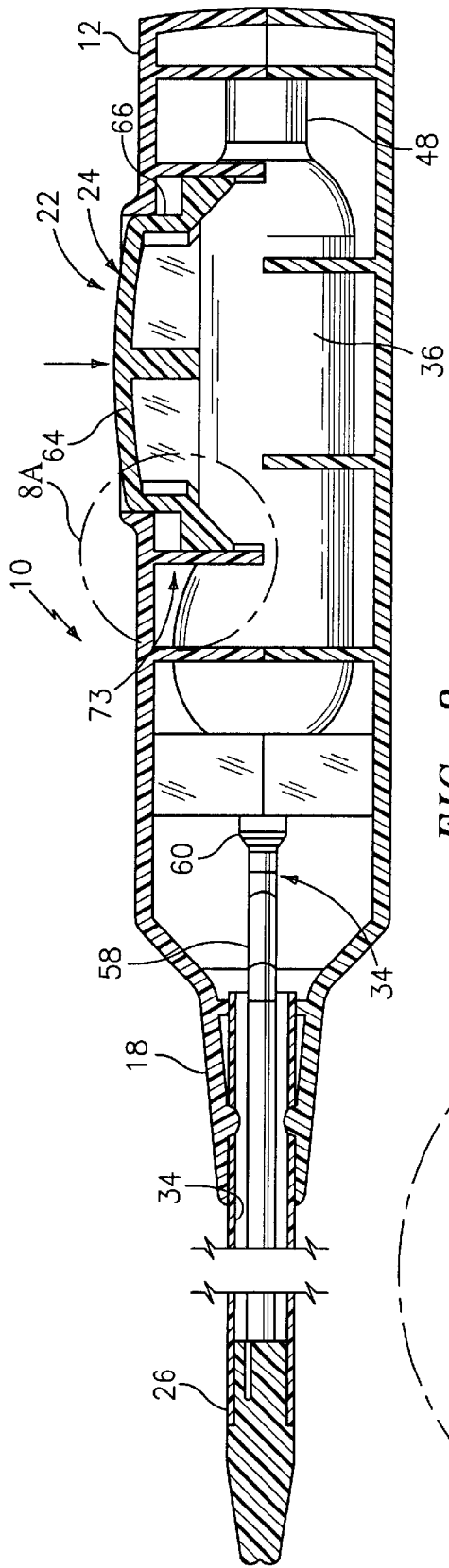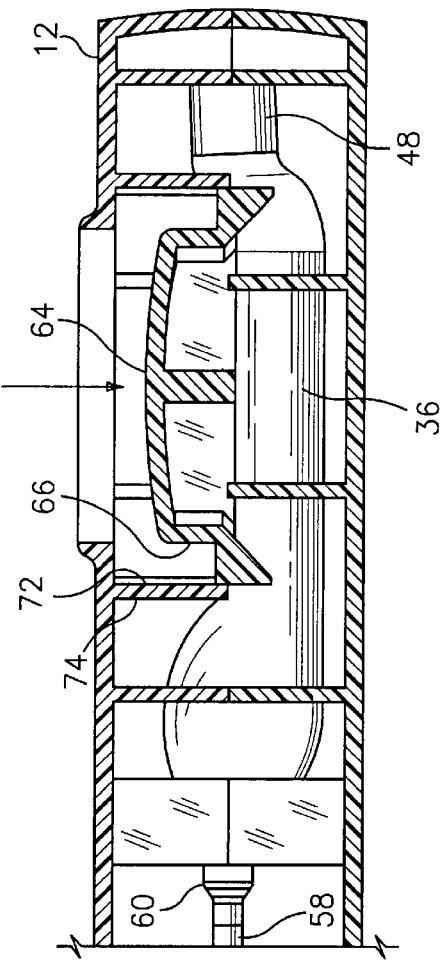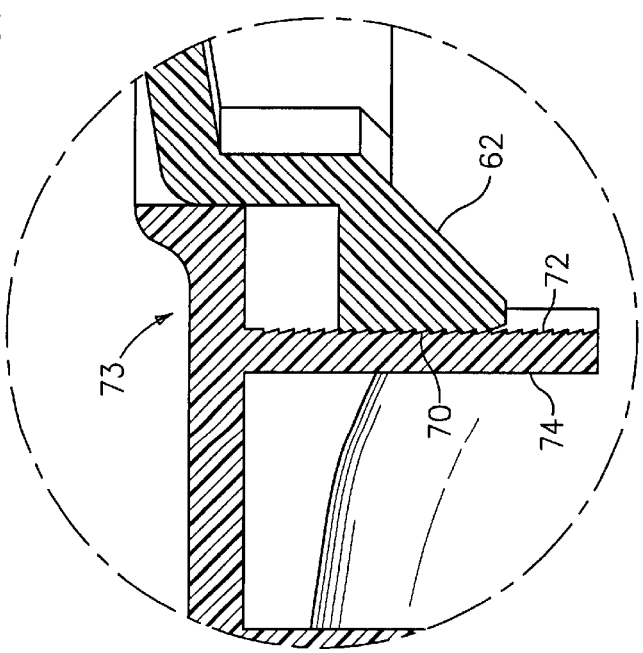

FIBRIN SEALANT APPLICATOR

BACKGROUND

1. Technical Field

The disclosure relates generally to an applicator for applying a tissue sealant based on human or animal proteins and more particularly to an apparatus for applying an adhesive formed by combining solutions of the proteins to tissues or organs for sealing wounds, stopping bleeding and the like.

2. Description of Related Art

A fibrin sealant is a biological adhesive formed by mixing two protein components, namely, fibrinogen and thrombin. Each protein component is derived from human plasma and is subjected to virus elimination procedures. The components are typically individually dehydrated and stored in separate vials as sterile freeze-dried powders.

It is known that purified fibrinogen and thrombin, together with a variety of known adjuvants, can be combined in vitro to produce a polymer having great potential benefit, both as a hemostatic agent and as a tissue adhesive. Because of the rapid polymerization upon intimate interaction of fibrinogen and thrombin, it is important to maintain these two blood proteins separate until applied at the application site. These protein solutions are generally delivered by devices such as a dual syringe apparatus.

One dual syringe apparatus for applying a fibrinogen-based tissue adhesive is disclosed in U.S. Pat. No. 4,359,049 to Redl et al. Redl et al. disclose a mechanism in which two standardized one-way syringes are held in a support having a common actuating means. The dispensing end of each syringe is inserted into a collection manifold where the two components are mixed. The components are then dispensed through a common needle capable of covering a limited area of the application site.

It is often desirable or necessary to cover a broad area of a wound, either to stop bleeding, to fix tissue or to prevent infection. It is also desirable to prevent the two components from mixing within the dispensing device.

Further, all known devices for dispensing solutions of fibrinogen and thrombin require the addition of these proteins in powdered form to the body of the syringe. This makes the proteins susceptible to contamination by impurities which may enter the syringe body. Further still, the use of the syringe body to mix the proteins with water to create the protein solutions can cause the solutions to leak out from either the dispensing end of each syringe or the proximal end of the syringe body.

Additionally, a dual syringe apparatus for the application of fibrinogen and thrombin solutions to an application site generally contains several parts, such as a syringe plunger, a "Y" manifold connector, a dispensing needle, a syringe holder, syringe needles, and conduits for transporting the solutions to the dispensing needle. Therefore, known fibrin sealant applicators, such as disclosed in U.S. patent to Redl et al. discussed above, and in U.S. Pat. No. 4,874,368 to Miller et al. and U.S. Pat. No. 4,979,942 to Wolf et al. are difficult to reuse. The replenishment of the protein components typically require removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, adding sterile water to each syringe, replacing the syringe plunger, replacing the plunger clip, and mixing the solutions. In an application where time is of the essence, such a lengthy replenishing process is impractical and cumbersome.

Furthermore, known applicators for dispensing a biological adhesive require the manual exertion of a force on the protein components so they can be dispensed from the applicator. Typically, a manual force is exerted on the components by means of the plunger in the standard one-way syringe. This type of arrangement is shown in U.S. Pat. No. 4,359,049 discussed above, and U.S. Pat. No. 4,631,055 to Redl et al. Manually exerting a force on a plunger located at proximal end of the applicator can make the application of the adhesive difficult. For example, the user is unable to clearly view the application site when holding the applicator perpendicularly to the application site. Further, such an arrangement causes air to enter the syringes causing difficulty in exerting a force via the syringe plunger.

Thus, there is a need in the art for a fibrin sealant applicator wherein the adhesive covers a broad area of a wound, either to stop bleeding, to fix tissue or to prevent infection. There is also a need for a fibrin sealant applicator wherein a manual force is applied via an activator assembly having a mechanism for preventing air from entering reservoirs containing the solutions. Further, there is a need for a fibrin sealant applicator wherein the adhesive components are not susceptible to contamination and the adhesive components are not intermixed within the applicator.

In addition, there is a need for a fibrin sealant applicator wherein the component solutions are easily replenished. There is also a need for a fibrin sealant applicator which is self-cleaning and reusable with different component solutions. Further, there is a need for a fibrin sealant applicator which is inexpensive to manufacture for allowing the applicator to be disposed of after use. Additionally, there is a need for a fibrin sealant applicator which avoids wasting adhesive solution and allows the application site to be clearly seen by the user when applying the component solutions perpendicular to the application site.

SUMMARY

An applicator is provided for dispensing a first and a second component of a biological adhesive. The applicator includes a housing having a housing head for enclosing therein a first reservoir containing the first component, and a second reservoir containing the second component. The housing further includes an elongated body portion defining a longitudinal axis for enclosing therein a conduit assembly having a first and a second conduit in communication with the first and second reservoir, respectively. An activator assembly is provided which includes an activator and a rachet mechanism for compressing the reservoirs within the housing to dispense the biological components into the conduits. An applicator tip having two separate channels in communication with the conduits may be provided on a distal end of the elongated body portion for dispensing the components at the application site. The first and second components are preferably fibrinogen and thrombin which intermix to form a fibrin sealant.

BRIEF DESCRIPTION OF THE DRAWINGS

Various embodiments are described herein with reference to the drawings, wherein:

FIG. 2A is an enlarged view of a rachet member on an activator assembly shown by FIG. 1;

FIG. 4 is a perspective view of the reservoir assembly depicted in FIG. 2;

FIG. 4A is a perspective view of the embodiment of FIG. 1 showing the placement of the reservoir assembly of FIG. 4 within the housing;

FIG. 5 is an enlarged view of an alternative embodiment of the reservoir assembly, FIG. 5A is a perspective view of an alternative embodiment of the applicator showing the placement of the reservoir assembly of FIG. 5 therein;

FIG. 7 is a cross-sectional view taken along line 7 in FIG. 3 showing the activator assembly in an inactivated state;

FIG. 7A is an enlarged view of the rachet mechanism;

FIG. 8 is a cross-sectional view showing the activator assembly in an activated state;

FIG. 8A is an enlarged view of the rachet mechanism guiding the activator;

FIG. 9 is a cross-sectional view showing the activator assembly in a fully compressed state;

DETAILED DESCRIPTION OF PREFERRED EMBODIMENTS

Figure 1:
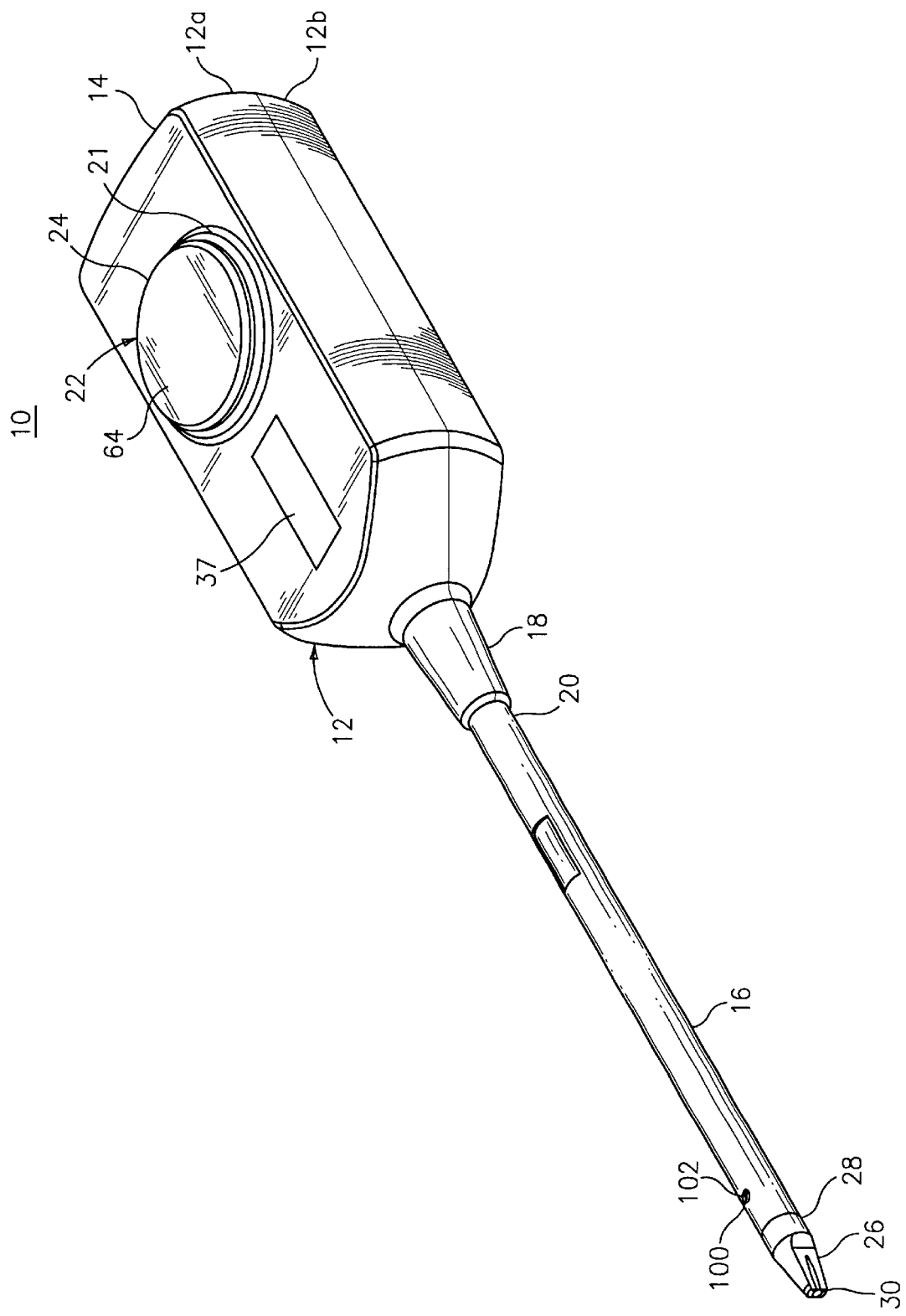
FIG. 1 is a perspective view of a preferred embodiment of a fibrin sealant applicator.

Referring to FIG. 1, a fibrin sealant applicator according to a preferred embodiment of the present disclosure is shown. The applicator designated generally by numeral 10 includes a housing 12 having a housing head 14 and an elongated body portion 16 defining a longitudinal axis. Housing head 14 contains a conically-shaped distal end 18 having a bore 20 in the center thereof dimensioned to receive body portion 16. While the housing head 14 is shown as being rectangular, it is understood that other shapes that contribute to the ease of gripping and controlling the applicator 10 may be used.

The housing head 14 includes an opening 21 for receiving an activator assembly 22 having an activator 24 for effectuating the dispensing of biological components as further described below. An applicator tip 26 is provided at a distal end 28 of the body portion 16 having two boresights 30 for dispensing biological components contained within housing head 14. In the preferred embodiment, the biological components are a fibrinogen solution and a thrombin solution which intermix to form a fibrin sealant. It is to be understood, however, that other biological fluids may be substituted, depending upon the choice of mixture that is to be dispensed.

Figure 2:
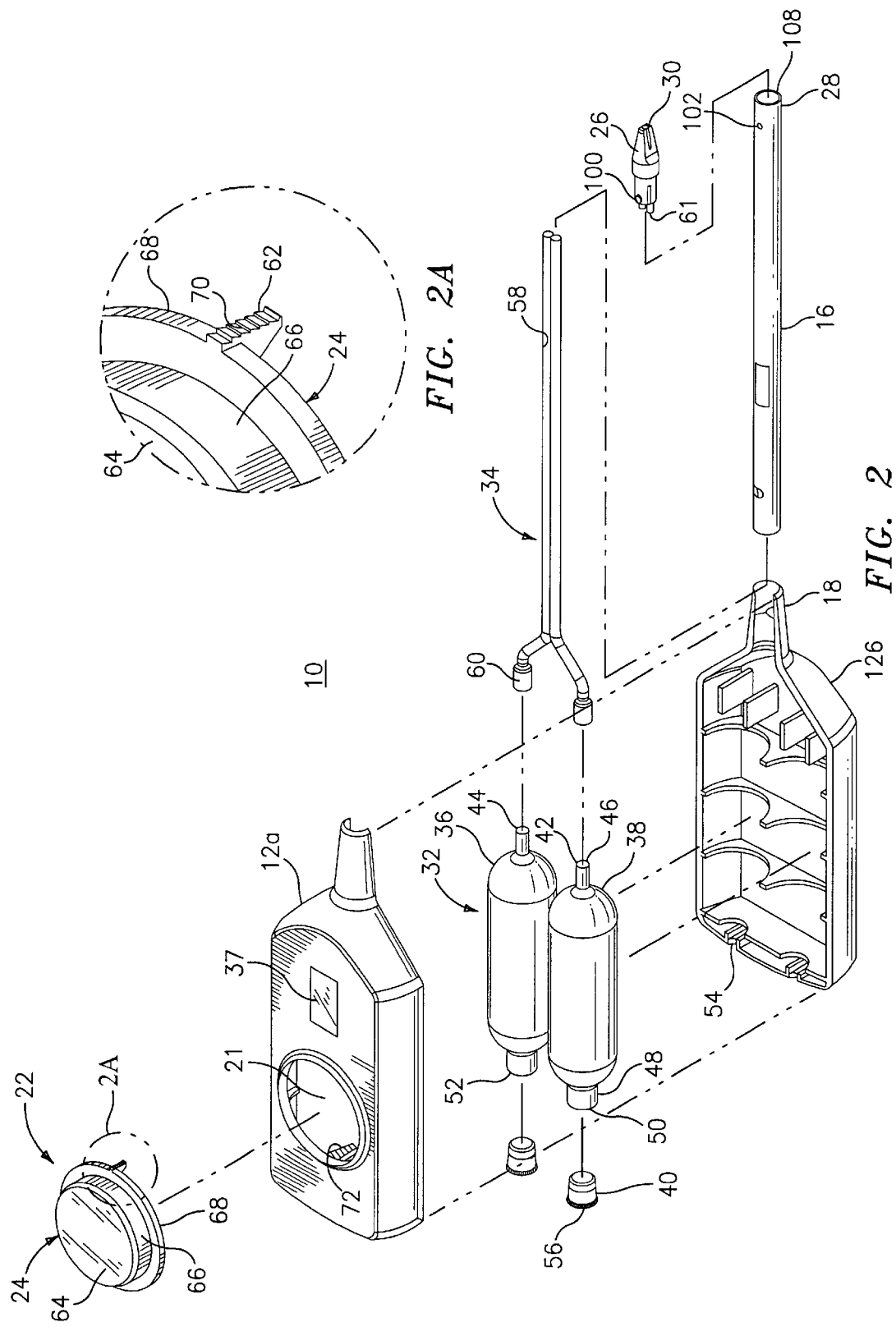
FIG. 2 is a perspective exploded view of the embodiment of FIG. 1.

The internal components of housing 12 will now be discussed in detail with reference to FIGS. 2–5A. As shown in FIG. 2, housing 12 is formed from molded housing half sections 12a and 12b which are formed with internal partitions configured to properly align the internal components of the applicator 10 with respect to each other and to prevent movement of the components. The internal components of the applicator 10 include a reservoir assembly 32 and a conduit assembly 34. The two assemblies are interrelated with each other and with the activator assembly 22 discussed above.

Reservoir assembly 32 includes a first reservoir 36 and second reservoir 38, and two plugs 40. First reservoir 36 and second reservoir 38 are preferably constructed from a flexible material and contain the first and second biological components, respectively. A window 37 on housing half-section 12a will permit a user to view the contents within the first reservoir 36 and second reservoir 38. First reservoir 36 and second reservoir 38 include a first cylindrical extension 42 having a central throughbore 44 at a distal end 46, a second cylindrical extension 48 having a central throughbore 50 at a proximal end 52. Central throughbore 50 is used for placing the biological components in the reservoirs 36 and 38. Plug 40 is used to vacuum seal central throughbore 50 to prevent contamination of the biological components. The plug 40 includes a silicon surface 56 capable of being penetrated by a syringe needle for adding a liquid, preferably sterile water, within reservoirs 36 and 38 to intermix with the biological components to form protein solutions. The protein solutions are dispensed on the application site, as further discussed below.

The conduit assembly 34 includes two conduits 58 each having a nozzle 60 for matingly engaging the cylindrical extension 42 on first reservoir 36 and second reservoir 38 for connecting conduit assembly 34 to reservoir assembly 32. The conduit assembly 34 is mounted within housing 12 as illustrated by the dotted lines in FIG. 2 Two phantom channels 61 within applicator tip 26, each leading to one of the two boresights 30, are preferably press fitted to the distal end of the conduits 58 for providing fluid communication between the conduit assembly 34 and the applicator tip 26.

FIG. 2A is an enlarged view of a portion of the activator assembly 22. As described in greater detail below, the activator assembly 22 controls the pressure exerted on reservoirs 36 and 38, and includes the activator 24 and a rachet member 62. The activator 24 includes an activation area 64, a shaft 66, and a disc 68. The shaft 66 connects the activation area 64 with the disc 68. The rachet member 62 extends downwardly from disc 68 and includes teeth 70 for engaging teeth 72 on an inner extension 74 of housing 12 to form structure for controlling the position of the activator 24. The control structure is a rachet mechanism 73. The rachet member 62 is preferably formed integral with the disc 68. Activator 24 may be formed with a transparent material or with a transparent window therein to permit viewing of the internal components of the applicator 10.

Figure 3:
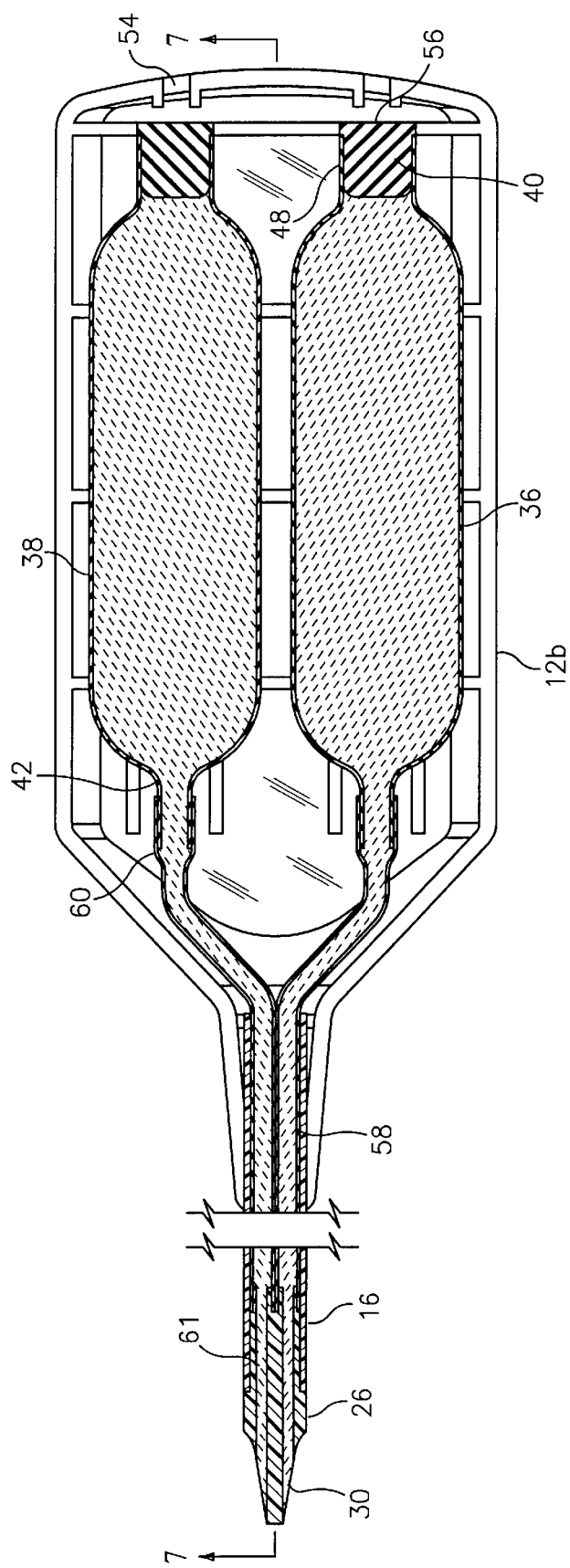
FIG. 3 is a cross-sectional top view of the embodiment of FIG. 1.

An assembled cross-sectional, top view of the applicator 10 illustrating the flow of the protein solutions is shown by FIG. 3. The protein solutions are kept separated to prevent intermixing and the creation of a fibrin sealant within the applicator 10. Upon exertion of pressure on activator 24, components are forced through conduit assembly 34 to applicator tip 26.

FIG. 4 illustrates a preferred embodiment of the reservoir assembly 32. The first reservoir and second reservoir 38 are identical for encasing an equal volumetric amount of their respective protein solution as compared to the other reservoir. It is contemplated to provide a different color for each reservoir 36 and 38 to easily recognize the reservoir containing fibrinogen and the reservoir containing thrombin. It is further contemplated to provide a different shape for each reservoir for the same purpose. However, the volumetric amount stored within the first reservoir 36 should be equal to the volumetric amount stored within the second reservoir 38 to maintain a predetermined fibrinogen to thrombin solution ratio, which is typically a 1:1 ratio.

A perspective view of the reservoir assembly 32 of FIG. 4 as placed within housing 12 is illustrated by FIG. 4A. It is contemplated that the first reservoir 36 and the second reservoir 38 are manufactured from a transparent plastic for being able to view the amount of solution and to determine if the solution has been sufficiently intermixed before being dispensed on the application site. It is further contemplated to provide calibration markings on the first reservoir 36 and second reservoir 38. It is additionally contemplated that reservoir assembly 32 is permanently affixed to the conduit assembly 34. In such an embodiment, the reservoir assembly 32 and the conduit assembly 34 can be disposed of after each use and new reservoir and conduit assemblies can be fitted to applicator 10.

FIGS. 5 and 5A illustrate an alternative embodiment of applicator 10 and reservoir assembly 32. Reservoir assembly 76 illustrated by FIG. 5 includes a first reservoir 78 and second reservoir 80 having cylindrical extensions 82 fitted with plugs 84 for sealing the components. The applicator illustrated by FIG. 5A and designated generally by numeral 86 is identical to applicator 10 without entry holes 54; with a different partition layout on housing half-section 12b and with a different connecting method for connecting reservoirs 78 and 80 with conduit assembly 88. Specifically, conduit assembly 88 includes nozzles 90 having a syringe needle (not shown) in a center thereof for penetrating surface 92 on plugs 84. The protein solution are dispensed to conduit assembly 94 via the syringe needles. Two mounts 96 are provided to conduit assembly 88 to create a force directed towards the proximal end of applicator 86 when reservoirs 78 and 80 are forced against the syringe needles to permit the syringe needles to penetrate surface 92 of each plug 84.

Figure 6:
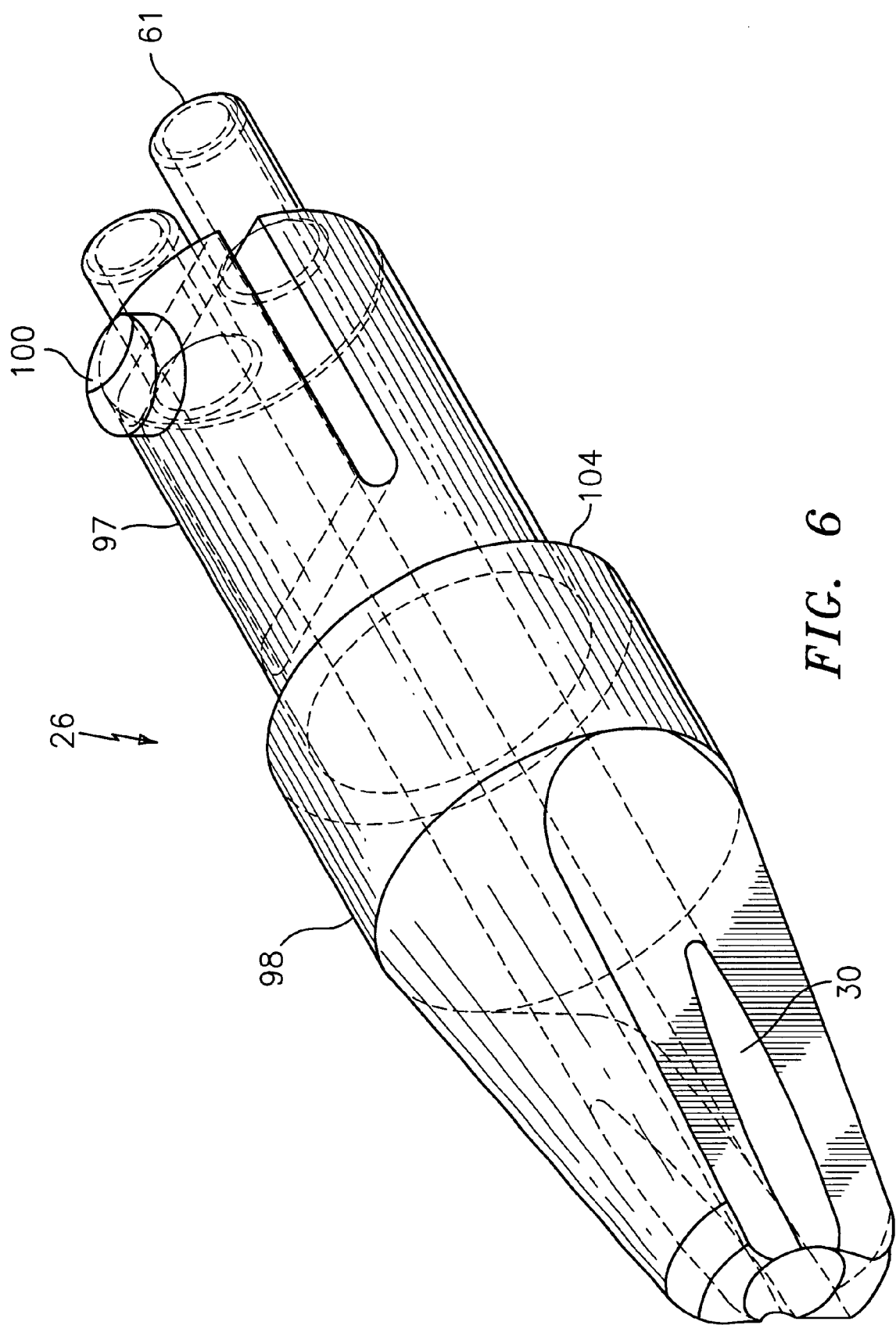
FIG. 6 is an enlarged perspective view of a preferred applicator tip having phantom channels and boresights for dispensing the components.

An enlarged view of the preferred embodiment of applicator tip 26 is illustrated by FIG. 6. The applicator tip 26 is preferably made from a metallic alloy capable of being sterilized and includes a cylindrical proximal end 97 and an applicator head 98. Further, as mentioned above, applicator tip 26 includes two channels 61 for matingly engaging conduits 58. Each channel 61 extends through the applicator tip 26 to one of the two boresights 30 for dispensing the protein solutions to the application site. The cylindrical proximal end includes a clasping button 100 for matingly engaging a hole 102 in body portion 16. When applicator tip 26 is connected to body portion 16, a circumferential surface 104 dividing the cylindrical proximal end 96 with the applicator head 106 is made flush with a distal end surface 108 of body portion 16.

The operation of applicator 10 will now be described in detail with reference to FIGS. 7–9. FIG. 7 depicts the applicator 10 with the activator 24 in an inactivated state As illustrated by FIG. 7A, the activator 24 is maintained in the inactivated state by the rachet mechanism 73 which has teeth 70 on rachet member 62 for lockingly engaging teeth 72 on the inner extension of 74 of housing 12.

Referring now to FIGS. 8 and 8A, there is illustrated the activator assembly 22 in an activated state. By exerting pressure to the activation area 64, the rachet mechanism 73 guides the activator 24 downwardly and the shaft 66 is forced further into the housing 12. As the shaft 66 enters the housing 12, the rachet mechanism 73 and the disc 68 compress reservoir 36 to dispense the protein solution via nozzle 60 into conduit assembly 34.

When ceasing to exert pressure to the activation area 64, the activator 24 is prevented from returning to the inactivated state by the rachet mechanism 73. As a result air cannot be sucked into the reservoirs 36 and 38 causing difficulty in further compressing reservoirs 36 and 38. Further, the position of the activator 24 with respect to housing half-section 12a provides a reference as to the amount of solution remaining in the first reservoir 36 and second reservoir 38. For example, when the activator 24 is in a fully activated state, as shown by FIG. 9, there is a small amount of solution left in the first 36 and second reservoir 38. Although the preferred embodiment has been described with a particular activator assembly, it is understood that other similar assemblies may be employed, as described below with reference to FIGS. 18–19B.

Figure 10:
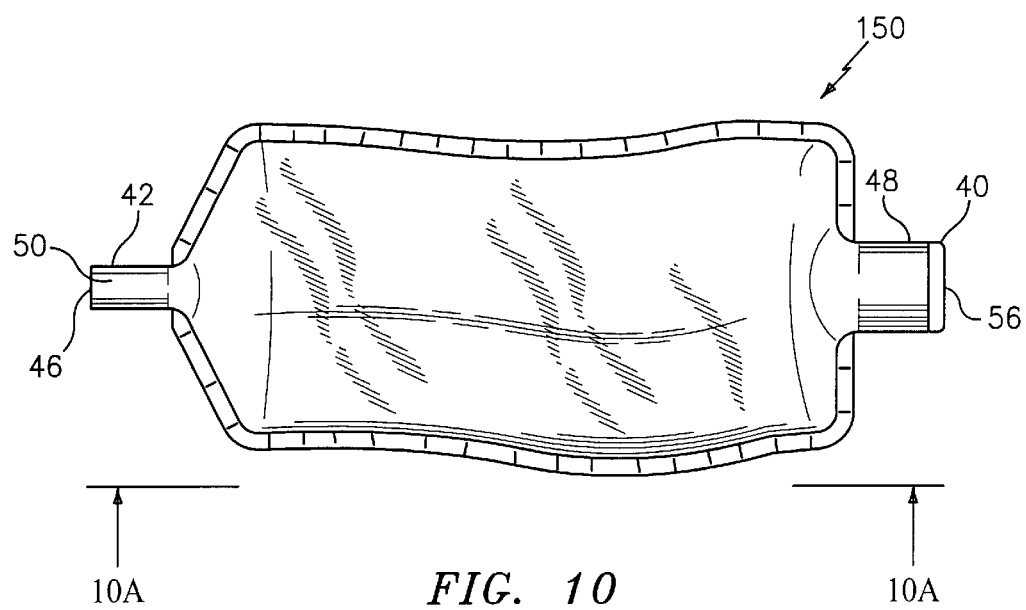
FIGS. 10–10B are enlarged views of an alternative collapsible reservoir.
Figure 10A:
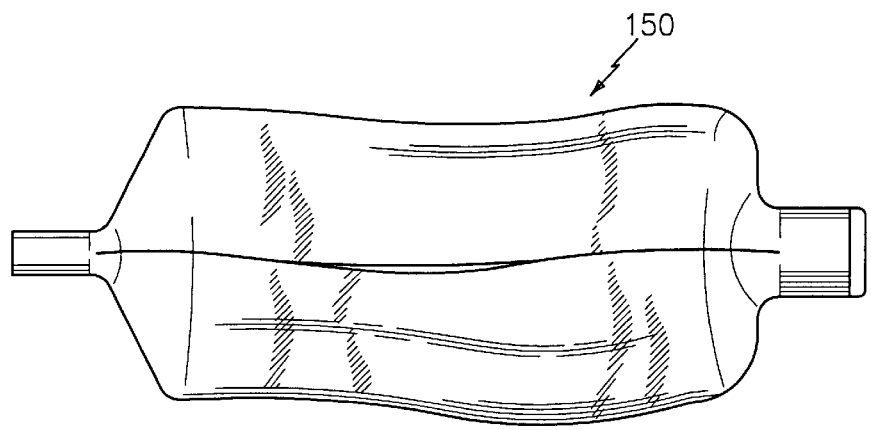
Figure 10B:
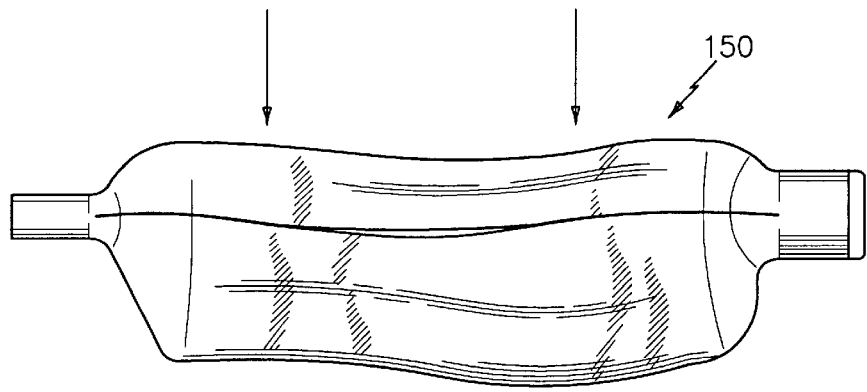

Referring to FIGS. 10–10B, there is illustrated an alternative embodiment of a reservoir designated generally by numeral 150. Reservoir 150, as reservoir 36, includes includes plug 40 to vacuum seal central throughbore 50 and the cylindrical extension 42 for connecting to the conduit assembly 34. However, unlike reservoir 36 which is constructed from a flexible material, reservoir 150 is constructed from a collapsible or nonflexible material which prevents the reservoir 150 from resuming its original, uncompressed shape as depicted by FIG. 10 after being compressed. As shown by FIGS. 10A and 10B, after the reservoir 150 is compressed, it does not resume its original, uncompressed shape.

Figure 11:
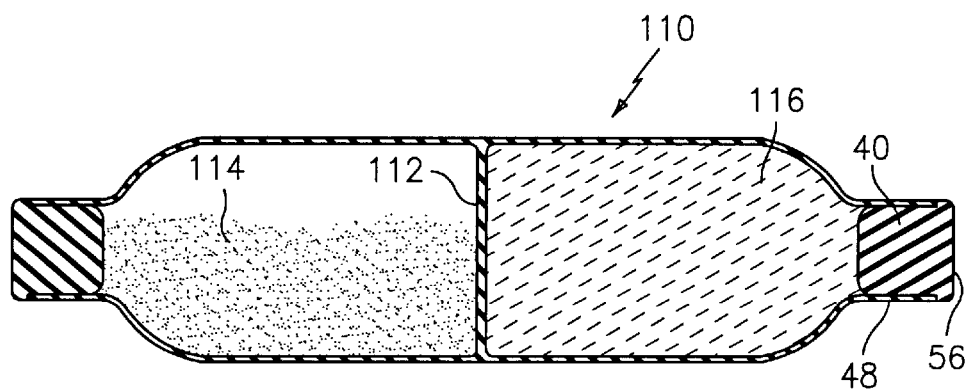
FIGS. 11–11A are cross-sectional views of an alternative reservoir having a frangible partition for separating a protein component from a liquid.
Figure 11A:
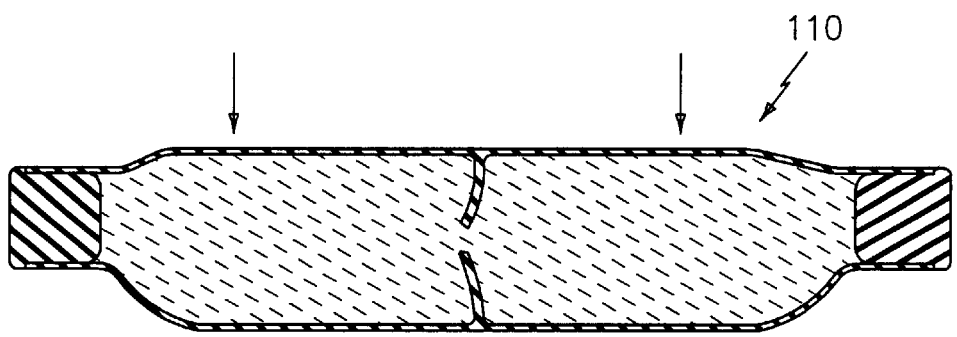

An alternative reservoir is illustrated by FIGS. 11 and 11A and is designated generally by numeral 110. Reservoir 110 is identical to reservoir 36, but with the addition of a frangible partition 112. The partition 112 separates the dehydrated protein 114 with the mixing liquid 116. The frangible partition 112 is broken by applying pressure to the collapsible reservoir 110, as indicated by the arrows in FIG. 11A, to mix the ingredients therein to form the protein solution.

Although four embodiments for the reservoirs have been illustrated and described, it is to be understood that the applicator 10 could be fitted with any of a number of different reservoirs, including, without limitation, syringes, bags or tubing. Furthermore, although the preferred embodiment for the reservoir assembly 32 has but two reservoirs, it is to be understood that additional reservoirs containing other solutions can be incorporated within applicator 10.

Figure 12:
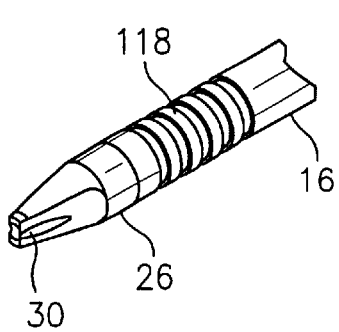
FIGS. 12–12A are perspective views of the distal end of the applicator having bellows for effectuating articulation of the applicator tip.
Figure 12A:
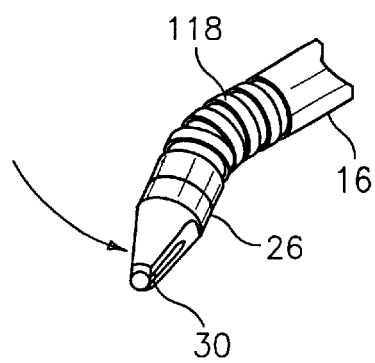

FIGS. 12–17 illustrate alternative embodiments for the distal end of applicator 10. FIGS. 12 and 12A illustrate body portion 16 being provided with bellows 118 for effectuating articulation of the applicator tip 26 for altering the dispensing angle with respect to longitudinal axis of the body portion 16.

Figure 13:
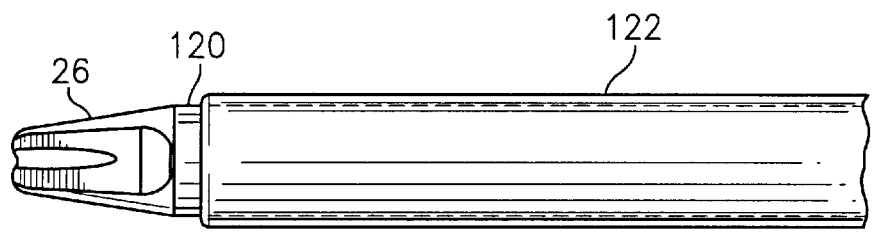
FIGS. 13–13A are perspective views of an alternative distal end of the applicator having a sleeve and a shape memory tube for varying the angular position of the applicator tip.
Figure 13A:
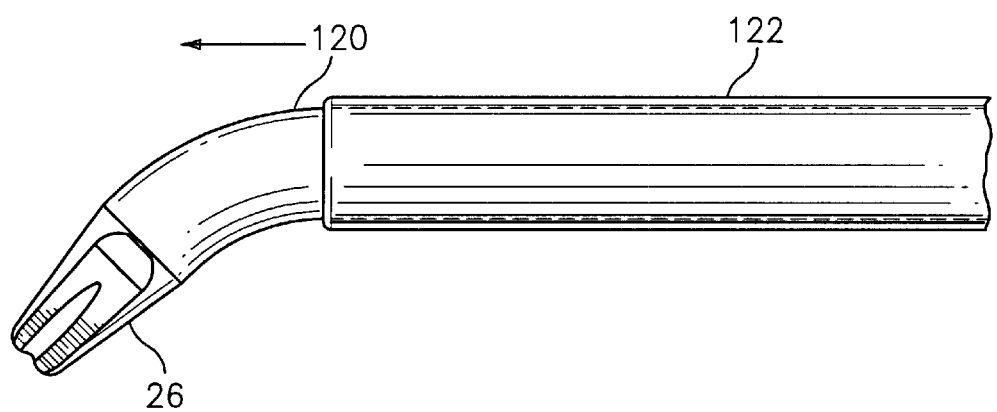

FIGS. 13 and 13A illustrate body portion 16 having shape memory metal 120 for altering the dispensing angle as sleeve 122 is moved proximally. The memory metal 120 resumes a straight configuration when sleeve 122 is pushed distally as shown by the arrow in FIG. 13A.

Figure 14:
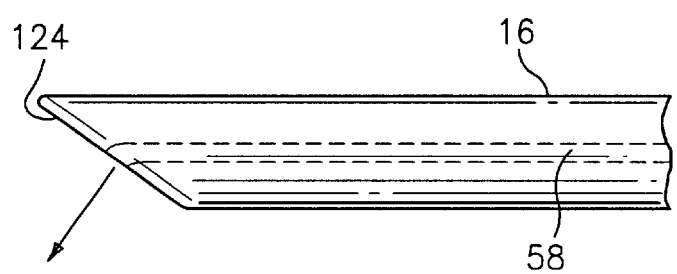
FIGS. 14–14A are perspective views of an alternative distal end of the applicator having an angular cut.
Figure 14A:
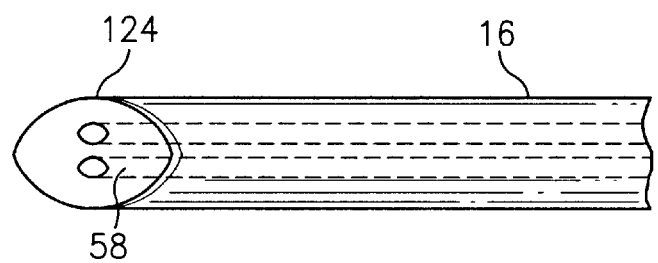

With reference to FIGS. 14 and 14A, there is illustrated another embodiment for altering the dispensing angle. In this embodiment, applicator tip 26 has been removed and the distal end of body portion 16 is provided with an angular cut 124 having approximately a 45° angle with respect to the longitudinal axis. The conduits 58 have curved distal ends to align with the 45° angular cut 124 for dispensing the protein solutions at a 45° angle from the longitudinal axis.

Figure 16:
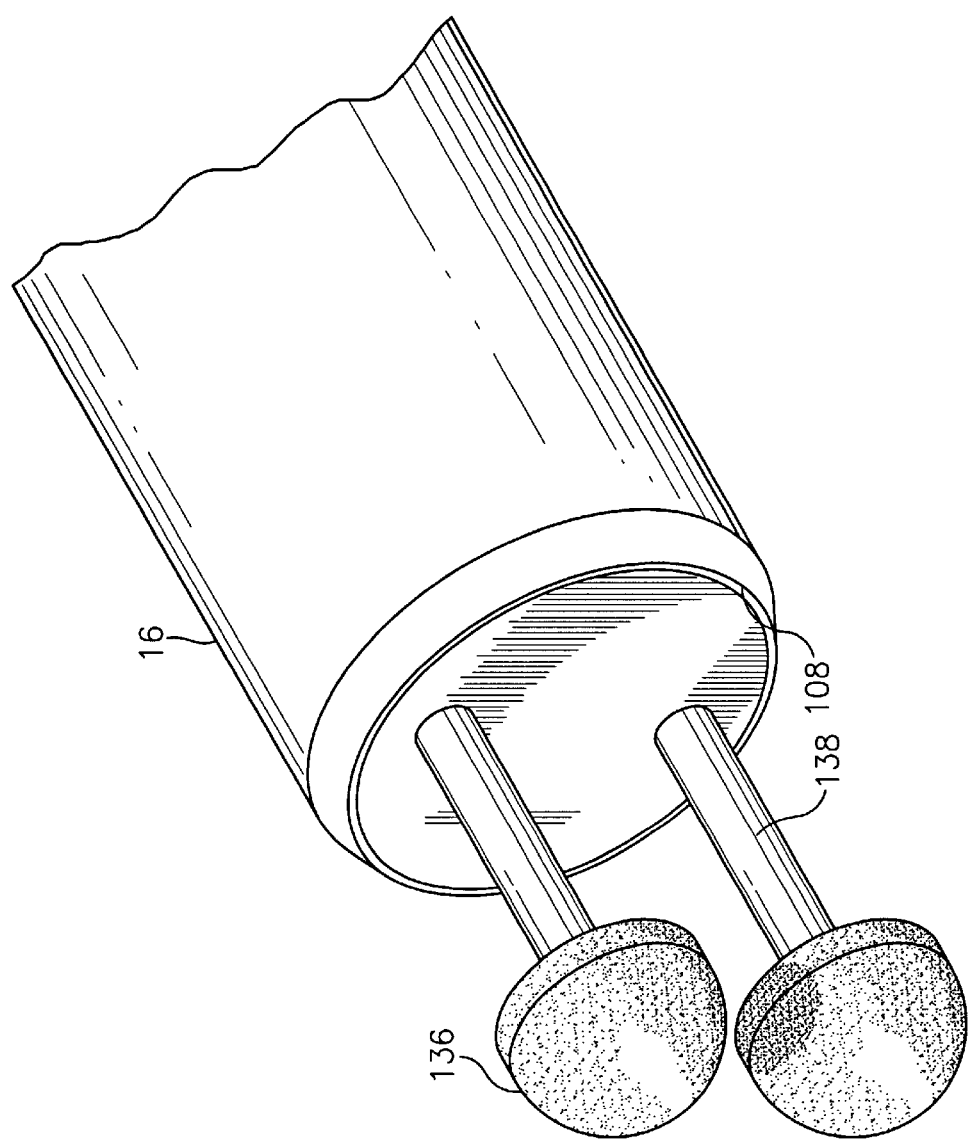
FIG. 16 is a perspective view of an alternative distal end of the applicator having an absorbable pad on each conduit.
Figure 15:
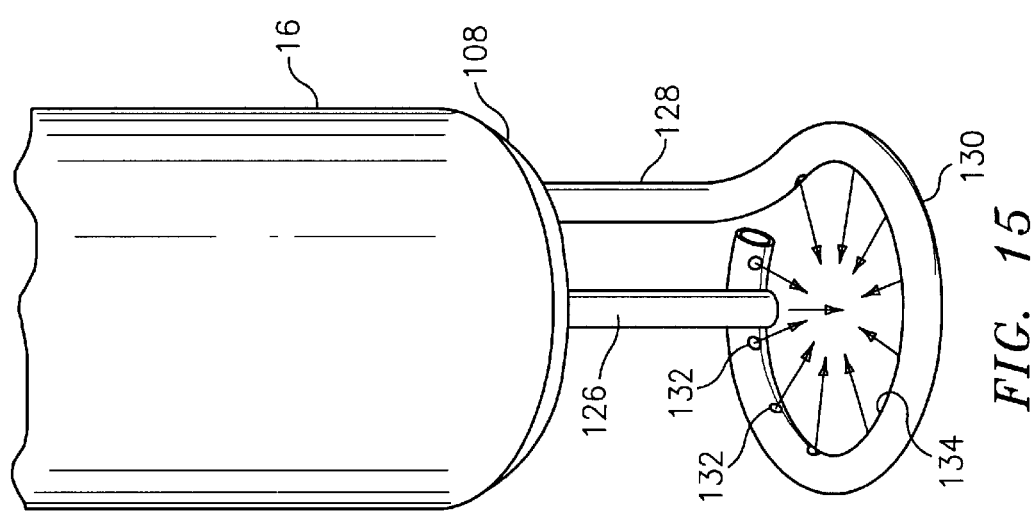
FIG. 15 is an enlarged view of an alternative distal end of the applicator having a straight and a circular conduit.

FIGS. 15 and 16 illustrate two additional alternative embodiments for the distal end of body portion 16. These embodiments include conduits which extend beyond the distal end of body portion 16.

The embodiment of FIG. 15 includes one straight conduit 126 and one conduit 128 having a circular configuration 130. The circular configuration 130 is provided with holes 132 on a side 134 facing the center of the circular configuration 130. One of the protein solutions exits the applicator 10 via holes 132 on conduit 128. This protein solution is intermixed with the protein solution which exits conduit 126. The embodiment of FIG. 15 is best suited for providing the fibrin sealant on small incisions or cuts which can be localized by circular configuration 130.

The embodiment of FIG. 16 includes pads 136 fitted at the distal end of conduits 138. The pads 136 are formed of a sponge-like material capable of absorbing the protein solutions. The pads 136 are used to spread the protein solutions on the application site. This embodiment is best suited for external wounds or larger internal site configuration.

Figure 17:
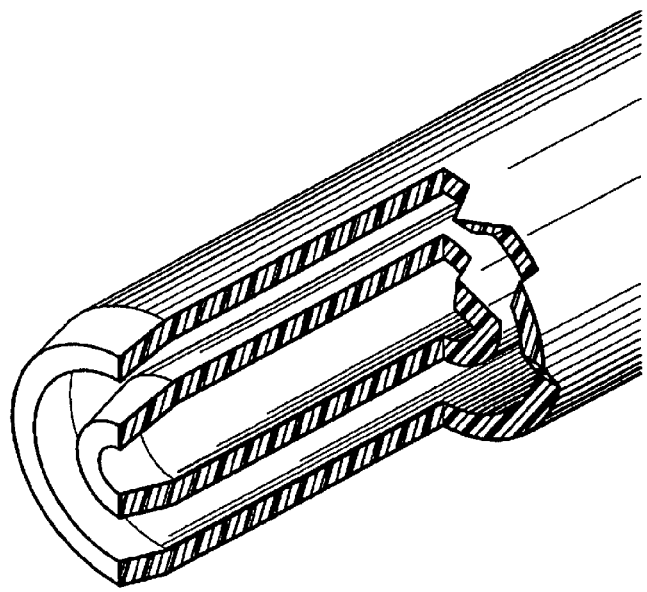
FIG. 17 is an enlarged view of the applicator having coaxial conduits.

With reference to FIG. 17, there is illustrated an alternative embodiment for body portion 16. Two coaxial paths 140 and 142 are formed within body portion 16. In this embodiment, a portion of conduits 58 are used to transport the protein solutions from the first 36 and second reservoir 38 to the proximal end of body portion 16 where they dispense the protein solutions within coaxial paths 140 and 142. The paths 140 and 142 transport the solutions to the application site. It is contemplated that the paths 140 and 142 have an identical volumetric capacity for transporting an equal amount of each solution to the application site.

As mentioned earlier, reference will now be made to two alternative embodiments for the activator assembly 22.

Figure 18:
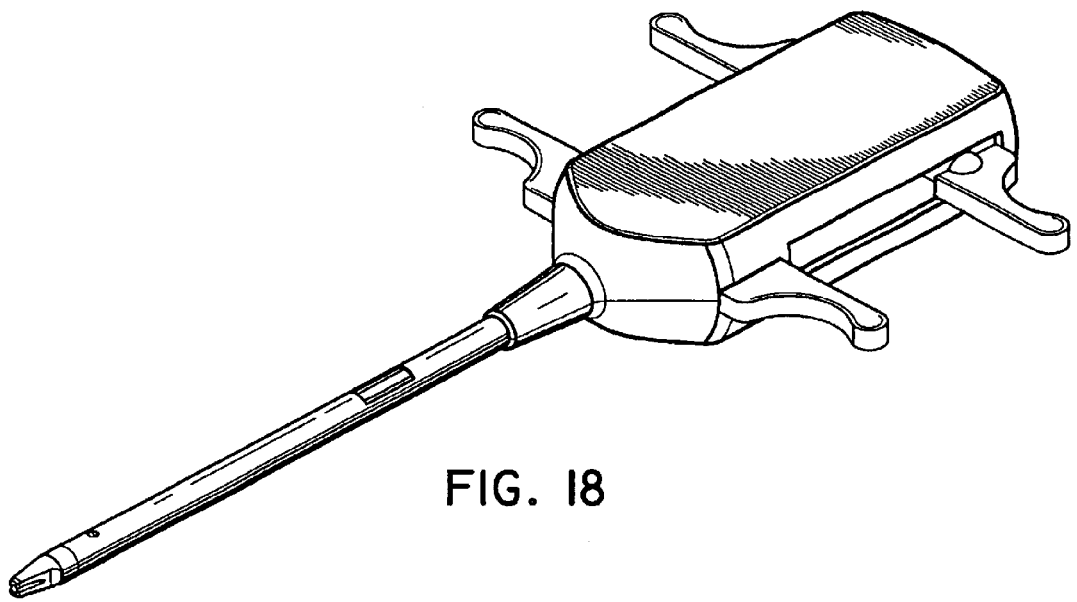
FIG. 18 is a perspective view of an alternative embodiment of the applicator having a drum activator in an inactivated state.

FIG. 18 illustrates an applicator designated generally by numeral 200 having a housing 202 including a housing head 204 and an elongated body portion 206. An applicator tip 208 is provided at a distal end 210 of body portion 206. An activator assembly 211 is provided on housing head 204 having a first and a second set of lateral finger grips 212 and 214. The first set on finger grips 212 is stationary and the second set on finger grips 214 is configured for movement along two horizontal slots 216 provided on each side of housing head 204.

Figure 18A:
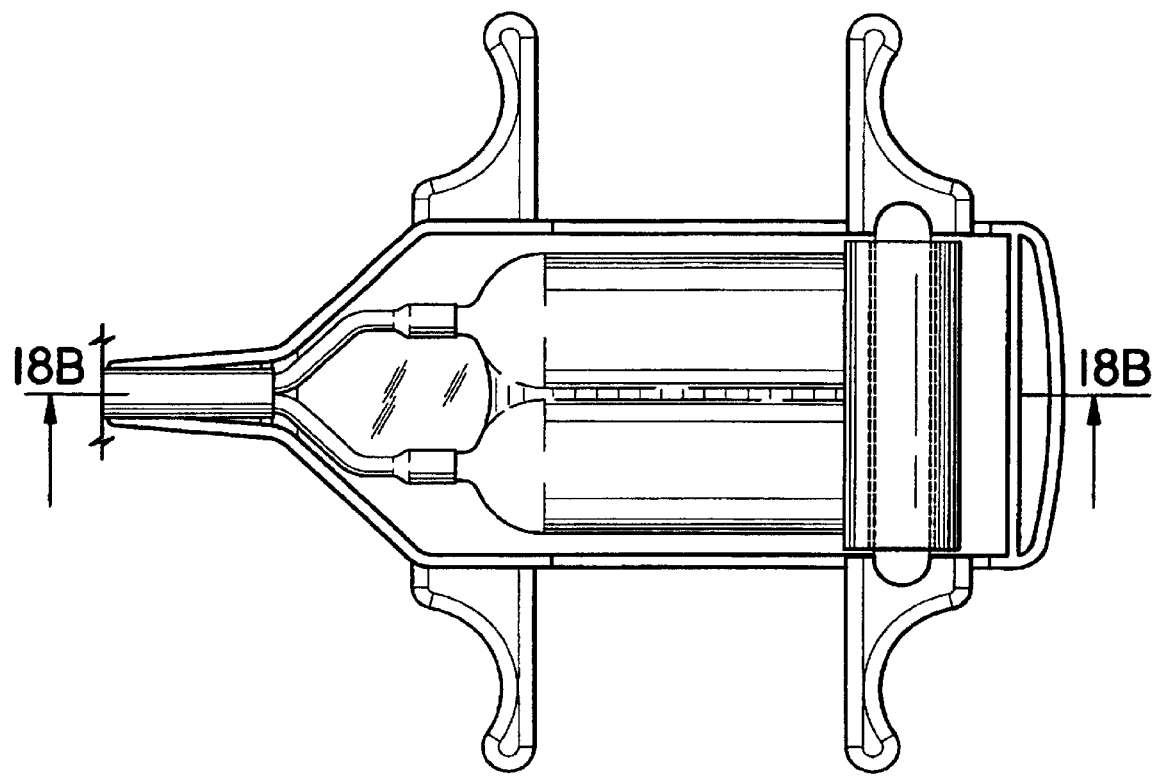
FIG. 18A is a top perspective view of the embodiment of FIG. 18.
Figure 18B:
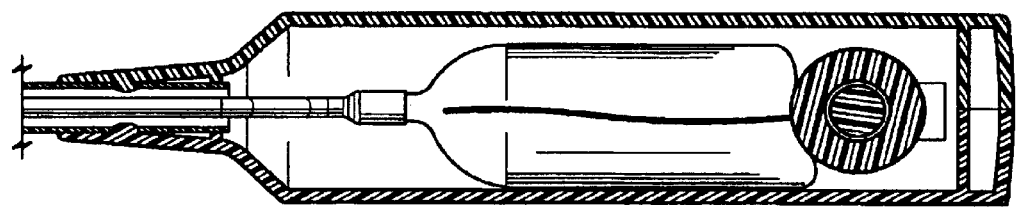
FIG. 18B is a cross-sectional view taken along line 18B in FIG. 18A.
Figure 18C:
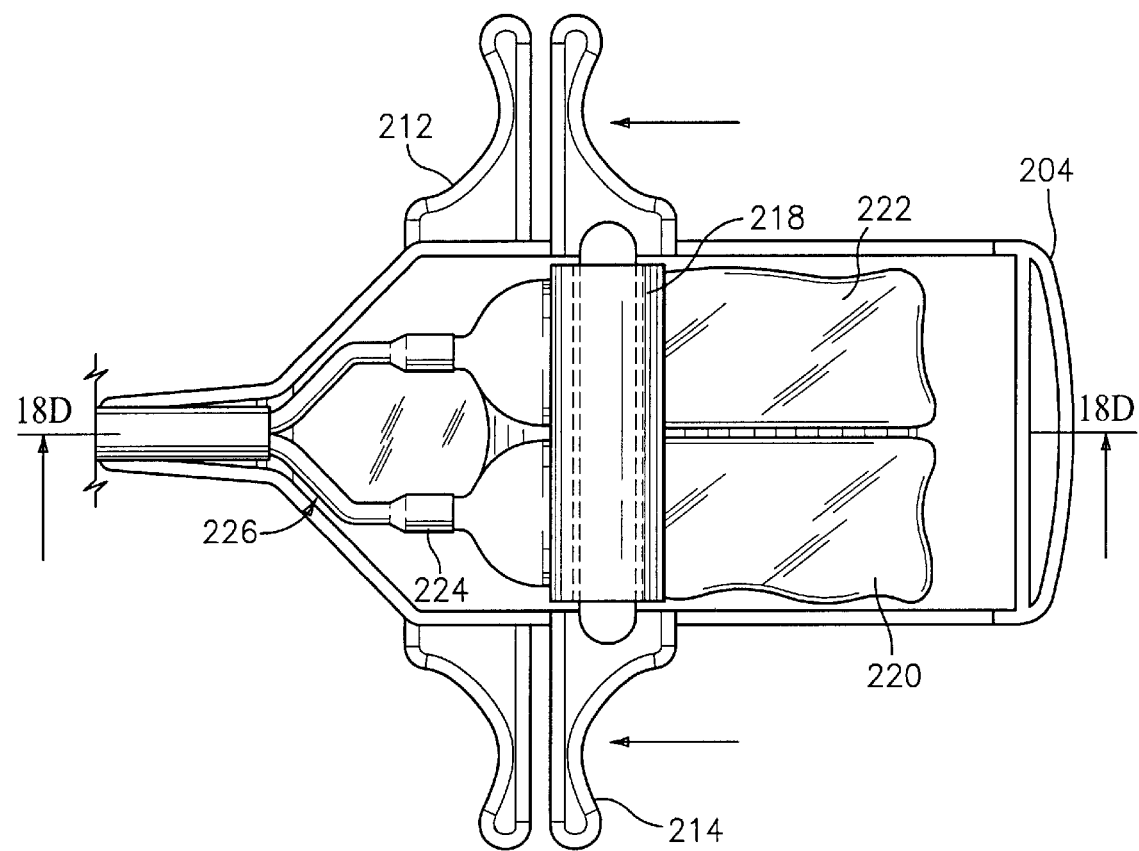
FIG. 18C is a top prospective view of the embodiment of FIG. 18 showing the drum activator in a fully activated state.
Figure 18D:
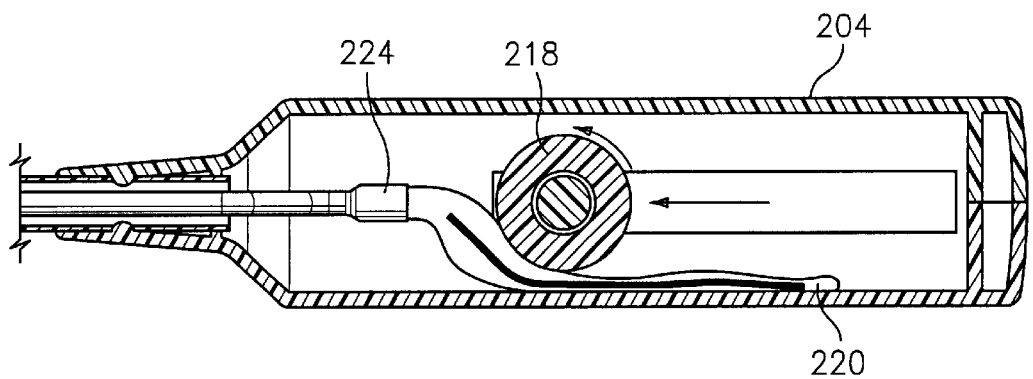
FIG. 18D is a cross-sectional view taken along line 18D in FIG. 18C.

With reference to FIGS. 18A and 18B, a cylindrical drum 218 is affixed to the second set of lateral finger grips 214. When the activator assembly 211 is in an inactivated state, as shown by FIGS. 18A and 18B, the drum 218 rests against the proximal end of reservoirs 220 and 222. In an activated state, as shown by FIGS. 18C and 18D, the second set of lateral finger grips 214 are brought towards the first set on finger grips 212. The forward lateral movement of the second set on finger grips 214 translates the drum 218 over reservoirs 220 and 222 to dispense the protein solutions via nozzles 224 to conduit assembly 226. The relative position of the second set of lateral finger grips 214 to the first set 212 provides a reference regarding the amount of solution remaining in each reservoir 220 and 222.

Figure 19:
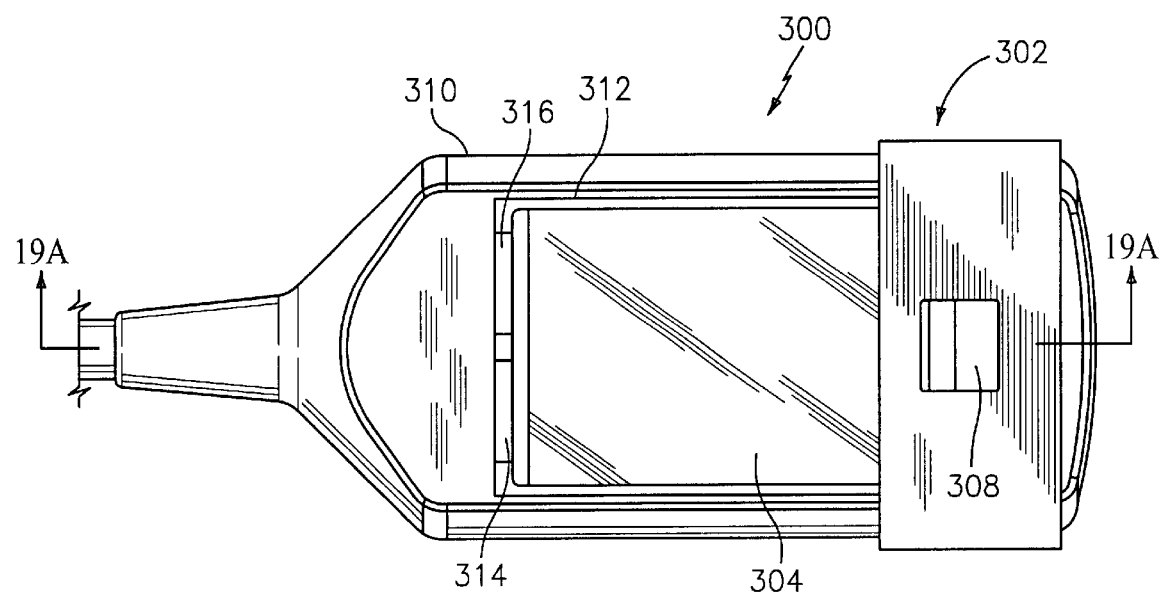
FIG. 19 is a perspective view of an alternative embodiment of the applicator having a hinged-plate activator.
Figure 19A:
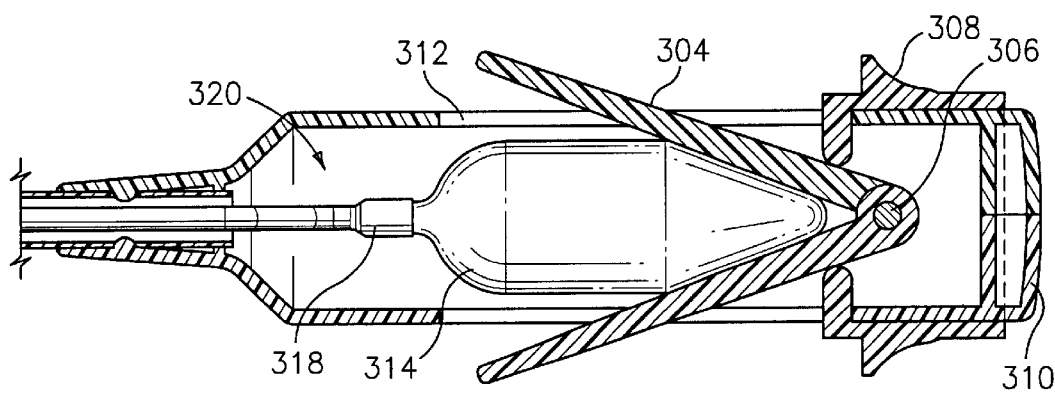
FIG. 19A is a cross-sectional view taken along line 19A in FIG. 19.
Figure 19B:
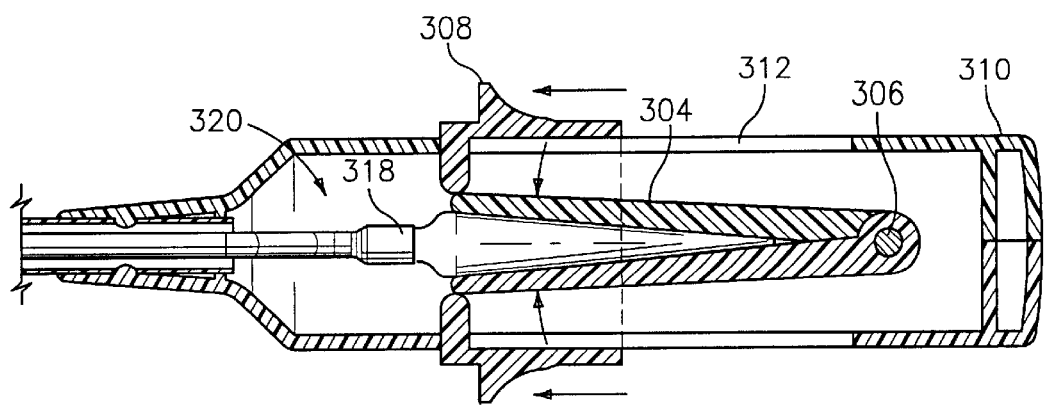
FIG. 19B is a cross-sectional view of the embodiment of FIG. 19 showing the hinged-plate activator in a fully activated state.

The second alternative embodiment for the activator assembly 22 will now be described with reference to FIGS. 19–19B, which depict an applicator designated generally by numeral 300. Applicator 300 includes an activator assembly 302 having a pair of hinged-plates 304 connected via hinge 306 and a slide 308. Housing 310 is provided with a cut-out portion 312 for guiding the slide 308 forward to create a plying action on reservoirs 314 and 316, as shown by the arrows in FIG. 19B, to dispense the protein solutions via nozzles 318 to conduit assembly 320. The relative position of the slide 308 along the cut-out portion 312 provides a reference regarding the amount of solution remaining in each reservoir 314 and 316.

It is also contemplated that conduits which have different diameters may be provided for allowing the biological components to be dispensed in different ratios. Further, an activator assembly may be provided which uses pressurized gas to dispense the components from the reservoirs.

Therefore, it is understood that various modifications may be made to the embodiments disclosed herein. For example, while specific preferred embodiments of the conduit, activator, rachet and reservoir assemblies, have been described in detail, structures that perform substantially the same function in substantially the same way to achieve substantially the same result can also be used. Also, besides applying a fibrin sealant, the fibrin sealant applicator can be used to preform human or veterinary surgical procedures including applying antiseptics, medication and other similar procedures. Therefore, the above description should not be construed as limiting, but merely as exemplifications of preferred embodiments. Those skilled in the art will envision other modifications within the scope and spirit of the claims appended thereto.

What is claimed is:

1. An applicator for dispensing a multicomponent biological adhesive, the applicator comprising:

a housing configured for operatively enclosing at least two self-contained collapsible reservoirs each having a sealable opening therein and storing at least one component of a multicomponent biological adhesive;

a conduit assembly extending from said housing and having a pair of conduits in fluid communication with said housing; and an activator assembly provided on said housing having an activator moveable from a first position to a second position within the housing to decrease the volumetric capacity of said housing and substantially and simultaneously compress the at least two self-contained collapsible reservoirs at a proximal end and a distal end to dispense at least one component through at least one of said pair of conduits to a distal end thereof, wherein the activator moves along a direction substantially perpendicular to a direction of fluid flow of the at least one component within a major portion of at least one of said pair of conduits.

2. The applicator of claim 1, further comprising an applicator tip having a pair of channels each being in fluid communication with said distal end of one of said pair of conduits.

3. The applicator of claim 1, wherein said activator assembly includes control structure for restricting said activator from returning to said first position after the activator is moved from said first position.

4. The applicator of claim 3 wherein said control structure includes a rachet mechanism.

5. The applicator of claim 1, wherein each of said pair of conduits include independent distal exits, such that said first and second components intermix external to said applicator.

6. The applicator of claim 1, wherein said housing defines a chamber configured to receive said at least one self-contained collapsible reservoir storing said at least one component of said mulitcomponent biological adhesive.

7. The applicator of claim 6 wherein said housing includes a housing head defining said chamber, said housing further including an elongated body portion extending from said housing head and housing a portion of said conduit assembly.

8. The applicator of claim 1, wherein said activator compresses said at least one self-contained collapsible reservoir as said activator is moved from said first position to said second position for dispensing said at least one component through said at least one of said pair of conduits to a distal end thereof.

9. An applicator for dispensing a first and a second component of a biological adhesive, the applicator comprising:
   a housing having at least one compartment configured for operatively receiving therein a first self-contained collapsible reservoir and a second self-contained collapsible reservoir;
   a first dispensing conduit in fluid communication with an interior chamber of said first self-contained collapsible reservoir when said first self-contained collapsible reservoir is operatively received by said housing for dispensing a first component provided within said interior chamber of said firs self-contained collapsible reservoir from a distal end of said first dispensing conduit;
   a second dispensing conduit in fluid communication with an interior chamber of said second self-contained collapsible reservoir when said second self-contained collapsible reservoir is operatively received by said housing for dispensing a second component provided within said interior chamber of said second self-contained collapsible reservoir from a distal end of said second dispensing conduit; and
   an activator assembly for exerting pressure on the first and second reservoirs as said activator assembly moves from a first position to a second position within the housing to decrease the volumetric capacity of said housing and to substantially and simultaneously compress the reservoirs at a proximal end and a distal end for dispensing the components provided within said interior chambers thereof to the dispensing conduits, wherein the activator assembly move along a direction substantially perpendicular to a direction of fluid flow of the first component within a major portion of the first dispensing conduit.

10. The applicator of claim 9 further comprising an applicator tip in communication with the dispensing conduits.

11. The applicator of claim 9 wherein said activator assembly exerts pressure on the reservoirs along a first axis to dispense first and second components within said first and second dispensing conduits, respectively, along a second axis.

12. The applicator of claim 9 wherein said dispensing conduits form coaxial paths within said housing.

13. A manually-operated applicator for dispensing a multicomponent biological adhesive, the applicator comprising:
   a conduit assembly having a pair of conduits;
   a collapsible reservoir assembly having a first self-contained collapsible reservoir containing a first adhesive component and a second self-contained collapsible reservoir containing a second adhesive component, the first reservoir being in communication with a first of said pair of conduits and the second reservoir being in communication with a second of said pair of conduits; and an activator assembly having an activator configured for movement from a first position to a second position within the housing for imparting pressure to said first and second self-contained collapsible reservoirs to substantially co press said first and second self-contained reservoirs along a radial axis thereof to effect dispensing of first and second adhesive components to said pair of conduits, wherein said activator contacts the first and second self-contained reservoirs and is fixed for movement along a single axis thereof.

14. The manually operated applicator of claim 13 wherein the conduit assembly and the reservoir assembly are supported within a single housing.

* * * * *